US006280986B1

(12) United States Patent
Hespell et al.

(10) Patent No.: US 6,280,986 B1
(45) Date of Patent: Aug. 28, 2001

(54) STABILIZATION OF PET OPERON PLASMIDS AND ETHANOL PRODUCTION IN BACTERIAL STRAINS LACKING LACTATE DEHYDROGENASE AND PYRUVATE FORMATE LYASE ACTIVITIES

(75) Inventors: Robert B. Hespell, deceased, late of Peoria, by David A Odelson, executor; Herbert A. Wyckoff, Roscoe; Bruce S. Dien, Peoria; Rodney J. Bothast, East Peoria, all of IL (US)

(73) Assignee: The United States of America as represented by the Secretary of Agriculture

( * ) Notice: Subject to any disclaimer, the term of this patent is extended or adjusted under 35 U.S.C. 154(b) by 0 days.

(21) Appl. No.: 09/201,449

(22) Filed: Nov. 30, 1998

Related U.S. Application Data (60) Provisional application No. 60/067,006, filed on Dec. 1, 1997.

(51) Int. Cl.[7] .............................. C12P 7/06; C12N 1/21; C12N 15/00
(52) U.S. Cl. ................. 435/161; 435/252.3; 435/252.33; 435/320.1
(58) Field of Search .................................... 435/243, 248, 435/252, 252.3, 252.33, 69.1, 190, 161, 320.1, 471, 476, 477; 562/479

(56) References Cited

U.S. PATENT DOCUMENTS

| 5,000,000 | 3/1991 | Ingram et al. | 435/161 |
|---|---|---|---|
| 5,424,202 | 6/1995 | Ingram et al. | 435/161 |
| 5,482,846 | 1/1996 | Ingram et al. | 435/161 |

OTHER PUBLICATIONS

Fairoz Mat–Jan et al. "Mutants of *Escherichia coli* Deficient in the Fermentative Lactate Dehydrogenase" *Journal of Bacteriology*, vol. 171, No. 1 (Jan. 1989) pp. 342–348.

R.B. Hespell et al. "Stabilization of pet Operon Plasmids and Ethanol Production in *Escherichia coli* Strains Lacking Lactate Dehydrogenase and Pyruvate Formate–Lyase Activities" *Applied and Environmental Microbiology*, vol. 62, No. 12 (Dec. 1996) pp. 4594–4597.

Wu, G. et al., Mutants *E. coli* affected in respiration...Journal of General Microbiology 139 (8), pp. 1795–1805, Apr. 1993.*

Ohta, K. et al. Genetic Improvement of *E. coli* ...Applied and Environmental Microbiology 57(4) pp. 893–900, Apr. 1991.*

* cited by examiner

*Primary Examiner*—Remy Yucel
*Assistant Examiner*—Lisa Gansheroff
(74) *Attorney, Agent, or Firm*—M. Howard Silverstein; Randall E. Deck; John D. Fado (57) ABSTRACT

Recombinant bacteria are disclosed which are transformed with heterologous DNA coding for alcohol dehydrogenase (adh) and pyruvate decarboxylase (pdc), and which are effective for use in the production of ethanol, but which do not require the presence of antibiotics in the culture medium to maintain genetic stability and high ethanol productivity. These recombinant bacteria are produced using mutant host strains which are substantially deficient in the ability to fermentatively reduce pyruvate. When grown in an anaerobic environment, the recombinant pyruvate mutants transformed with the adh and pdc genes are genetically stable, maintaining the inserted genes and ethanol productivity even in the absence of antibiotics.

10 Claims, 5 Drawing Sheets

STABILIZATION OF PET OPERON PLASMIDS AND ETHANOL PRODUCTION IN BACTERIAL STRAINS LACKING LACTATE DEHYDROGENASE AND PYRUVATE FORMATE LYASE ACTIVITIES

CROSS REFERENCE TO RELATED APPLICATION

This application hereby claims the benefit of U.S. provisional application No. 60/067,006 filed on Dec. 1, 1997, the contents of which are incorporated by reference herein.

BACKGROUND OF THE INVENTION

1. Field of the Invention

The invention relates to improved recombinant bacteria transformed with heterologous DNA coding for alcohol dehydrogenase and pyruvate decarboxylase, which are effective for use in the production of ethanol.

2. Description of the Prior Art

In the last decade, a major goal of biofuels research has been to metabolically engineer microorganisms to ferment multiple sugars from biomass or agricultural wastes to fuel ethanol. L. O. Ingram and his colleagues were first to report a metabolically engineered bacterium for high levels of alcohol production (U.S Pat. Nos. 5,000,000; 5,424,202; and 5,482,846). The cloned *Zymomonas mobilis* genes for pyruvate decarboxylase (pdc) and alcohol dehydrogenase (adh) were combined to form the PET operon which was transformed into *Escherichia coli* on pUC-based plasmid to form pLOI295 (Ingram et al., 1987, Appl Environ. Microbiol., 53:2420–2425). The resultant recombinant strain produced over 3.4% wt/v ethanol from glucose in media containing ampicillin (Amp) with positive selection pressure for the plasmid. PET operon plasmids and gene expression were improved by changes in promoters (Ingram and Conway, 1988, Appl. Environ. Microbiol., 54:397–404), insertion of a tetracycline (Tc) gene to form pLOI297 for plasmid selection and selection of hardier *E. coli* strains (Alterthum and Ingram, 1989, Appl. Environ. Microbiol., 55:1943–1948). Although the last workers showed *E. coli* B maintained pLOI297 for 25 generations in the absence of Tc, we have found rapid plasmid losses after this time and recently Lawford and Rousseau (1995, Biotechnol. Lett., 17:751–756; and 1995, Appl. Biochem. Biotechnol., 57/58:277–292) have shown even more rapid declines in levels of ethanol production. A considerably more stable strain was developed by Ohta et al. (1991, Appl. Environ. Microbiol., 57:893–900) by integrating the PET operon and chloramphenicol (Cm) resistance gene into the *E. coli* chromosome. The resultant *E. coli* strains did not require Cm in the growth media for retention of the PET operon, but ethanol production levels were much lower in the absence of Cm, presumably due to reduced PET gene copy number. When mutants were selected for resistance to high levels (600 µg/ml ) of Cm, high levels of ethanol production were restored as shown with strain KO11. However, Lawford and Rousseau (ibid) have found that these mutants also lose the ability to produce high levels of ethanol in the absence of Cm.

Although the bacteria genetically engineered to contain the PET operon produce high levels of ethanol, these recombinants require antibiotics in the growth media to maintain genetic stability and high ethanol productivity. In the absence of such antibiotics the bacterial population rapidly lose the ability to produce high levels of ethanol.

SUMMARY OF THE INVENTION

We have now discovered recombinant bacteria transformed with heterologous DNA coding for alcohol dehydrogenase (adh) and pyruvate decarboxylase (pdc), which are effective for use in the production of ethanol, but which do not require the presence of antibiotics in the culture medium to maintain genetic stability and high ethanol productivity. These recombinant bacteria are produced using mutant host strains which are substantially deficient in the ability to fermentatively reduce pyruvate. When grown in an anaerobic environment, the recombinant pyruvate mutants transformed with the adh and pdc genes are genetically stable, maintaining the inserted genes and ethanol productivity even in the absence of antibiotics.

In accordance with this discovery, it is an object of this invention to provide improved recombinant bacteria that are effective for use in the production of ethanol.

It is also an object of this invention to provide recombinant bacteria that are genetically stable and maintain high ethanol productivity in an anaerobic environment in the absence of antibiotics or other chemical selective agents.

Other objects and advantages of this invention will become readily apparent from the ensuing description.

DETAILED DESCRIPTION OF THE INVENTION

As noted hereinabove, Ingram et al. (U.S. Pat. Nos. 5,000,000; 5,424,202; and 5,482,846, the contents of each of which are incorporated by reference herein) disclosed the production of recombinant bacteria produced by transformation of bacterial hosts with heterologous genes encoding alcohol dehydrogenase (adh) and pyruvate decarboxylase (pdc). These recombinant bacteria are capable of producing significant amounts of ethanol as a fermentation product. To maintain genetic stability and high ethanol productivity, it has previously been necessary to grow the recombinant bacteria in the presence of antibiotics. The instant invention provides improved recombinant bacteria transformed with the adh and pdc genes, which do not require the presence of antibiotics in the culture media to maintain genetic stability and/or high ethanol productivity.

The recombinant bacteria of this invention are produced using bacterial hosts which are mutants substantially deficient in the ability to fermentatively reduce or metabolize pyruvate under anaerobic conditions. Mutants lacking the ability to fermentatively reduce pyruvate are typically incapable of anaerobic growth. However, we have surprisingly discovered that when these mutant hosts are transformed with the genes coding for alcohol dehydrogenase (adh) and pyruvate decarboxylase (pdc), the resultant recombinant bacteria are capable of anaerobic growth. The ability of the recombinant bacteria to grow in an anaerobic environment may be used to maintain a positive selective pressure for cells containing the adh and pdc genes. When the bacteria are grown in an anaerobic environment, only cells which retain the adh and pdc genes are capable of growth; any cells losing the genes are unable to grow and divide. Thus, the recombinant bacteria of this invention are quite stable anaerobically for ethanol production. The recombinants also do not require antibiotics in the growth media to maintain positive selective pressure for cells containing the adh and pdc genes because loss of the genes would be a conditionally lethal event.

Bacterial hosts suitable for use herein are prepared by preparation of mutants which are substantially deficient or lacking in the ability to fermentatively reduce pyruvate under anaerobic conditions. Those mutants are selected wherein the extent of mutation in pyruvate reduction activity renders the mutants incapable of anaerobic growth, in contrast to the parent strains which are capable of growth under anaerobic conditions.

In the preferred embodiment, such pyruvate mutant hosts are obtained by producing mutants substantially deficient in both lactate dehydrogenase (ldh) activity and pyruvate formate lyase (pfl) activity. Without being limited thereto, techniques for the production of double ldh⁻ and pfl⁻ mutants were previously described by Mat-Jan et al. (1989, J. Bacteriology, 171:342–348, the contents of which are incorporated by reference herein), and the techniques and double mutants described therein are suitable for use herein.

Mutation of the parent strains may be induced by treatment thereof with mutagens known in the art, with a variety of conventional mutagens which are effective for inducing random mutations in the genotype being suitable for use herein. These mutagens include, but are not limited to, ultraviolet irradiation, X-ray irradiation, or chemical mutagens including base analogs such as 5-bromouracil or 2-aminopurine, deaminating agents such as nitrous acid or hydroxylamine, alkylating agents such as ethyl methanesulfonate or nitrosoguanidine (N-methyl-N'-nitro-N-nitrosoguanidine), or acridine derivatives, or combinations of any of the above. Alternatively, mutations may be introduced by conventional genetic recombination (e.g. chromosomal insertion). The methodology of inducing mutations in the parent strains may be readily determined by the practitioner skilled in the art, and will of course vary with the specific mutagen selected. Conventional mutagenesis procedures which are suitable for use herein have been described, for example, by Miller (Experiments in Molecular Genetics, Cold Spring Harbor Laboratory, 1972, pp. 111–185), Esser and Kuenen (Genetics of Fungi, Springer Verlag, N.Y., 1967, pp. 266–294), or Davis et al. (Microbiology: Including Immunology and Molecular Genetics, Harper & Row, Hagerstown, Md. 1973, pp. 254–259), the contents of each of which are incorporated by reference herein.

In accordance with the preferred embodiment, cells of a parent bacterial strain are subjected to mutagenic treatment effective to induce mutation of the ldh and pfl encoding genes. These enzymes provide the predominant alternative pathways for the formation of terminal fermentation products for facultative anaerobic bacteria grown under anaerobic conditions. Subsequent to mutagenesis, the resultant strains are cultured and screened to select the specific colony or colonies which are deficient for the ldh and pfl activities. Generation of the mutations in each of the ldh and pfl genes and selection of the respective mutants may be conducted consecutively or simultaneously.

Cells with disrupted pfl activity may be isolated by selecting for cells that do not produce formate but which convert formate (added exogenously) to hydrogen and carbon dioxide. Preferred techniques for detecting pfl⁻mutants include the absence of $H_2$ gas or formate production, and use of benzyl viologen (BV) medium as described by Varenne et al. (1975, Mol. Gen. Genet., 141:181–184) or Chippaux et al. (1972, J. Bacteriology, 110:766–768), the contents of each of which are incorporated by reference herein. Pfl⁻ mutants produce colorless colonies under $N_2$ and/or $H_2$ atmosphere while wild-type colonies produce dark violet colonies. Pfl⁻ mutants which are also defective in ldh activity may be readily isolated as described by Mat-Jan et al. (1989). In brief, mutated cells are selected which are able to grow aerobically on solid culture media having glucose plus acetate as carbohydrates, but which will not grow anaerobically. Of course, it is also understood that ldh and pfl activity may also be quantitatively assayed using conventional enzyme assay techniques such as described by Tarmy and Kaplan (1968, J. Biol. Chem., 243:2579–2586) and Knappe (1969, Euro. J. Biochem., 11:316–327), respectively, the contents of each of which are incorporated by reference herein.

In an alternative embodiment, mutant bacterial hosts deficient in the ability to fermentatively reduce pyruvate may be obtained by mutagenesis of facultative anaerobic parent bacterial strains using the same techniques described above for the production of ldh⁻ and pfl⁻ mutants. Presumptive pyruvate mutants may be isolated by replica plating treated cells for culture on conventional solid media under aerobic and anaerobic conditions. Cells that are unable to grow anaerobically on conventional solid culture medium (but which grow aerobically) are retained as presumptive pyruvate mutants. Presumptive mutants may then be transformed with a suitable plasmid containing the heterologous genes encoding adh and pfc as described by Ingram et al. (U.S. Pat. Nos. 5,000,000; 5,424,202; and 5,482,846) and in the Examples hereinbelow. Transformants containing the plasmid and which are capable of anaerobic growth may then be retained for subsequent use.

In another alternative embodiment, bacterial cells may be transformed prior to mutagenesis and screening. In this embodiment, the parent bacterial strains may be transformed with an adh and pfc containing plasmid which also includes a selectable antibiotic resistance marker such as described by Ingram et al. and in the Examples. Pyruvate mutants may then be produced by mutagenesis as described above. Following mutagenesis, treated cells may be first cultured anaerobically on conventional solid media, and subsequently cultured anaerobically on media containing antibiotics. colonies growing on the media are selected as presumptive pyruvate⁻ transformants. Presumptive cells may be repeatedly cultured and tested for presence of the plasmid to ensure stability.

Transformation of the above-described mutant bacterial hosts with the heterologous DNA encoding adh and pdc may be conducted using the techniques described in detail by Ingram et al. (U.S. Pat. Nos. 5,000,000; 5,424,202; and 5,482,846) and in the Examples hereinbelow. In summary, as disclosed by Ingram et al. the genes encoding the adh and pdc may be obtained from many different sources and may be transformed into different hosts and expressed therefrom using a variety of promoters. In the preferred embodiment, the adh and pdc genes together with appropriate regulatory sequences may be incorporated into one or more plasmids suitable for use with the bacterial host of interest. In a particularly preferred embodiment, the source of the adh and pdc genes is the PET operon wherein the adh and pdc genes are derived from *Zymomonas mobilis*. Furthermore, genes encoding for one or more polysaccharases may be optionally added to the same or a different plasmid to enable the transformed cells to utilize complex substrates.

The invention may be practiced using a variety of gram negative bacteria. Preferred bacteria for use herein include facultative anaerobic bacteria, most preferably facultative gram negative bacteria, and particularly bacteria of the family Escherichiaceae, such as Escherichia, Erwinia, and Klebsiella species. Other bacteria which are suitable for use herein include those described by Ingram et al. (U.S. Pat. Nos. 5,000,000; 5,424,202; and 5,482,846).

The recombinant bacteria of this invention are effective for the fermentation of a variety of sugars from biomass or agricultural wastes to ethanol using conventional techniques. Many processes for the fermentation of monomeric sugars such as glucose generated from lignocellulose are well known, and are suitable for use herein. In brief, the cellulytic material may be enzymatically, chemically, and/or physically hydrolyzed to a glucose or other monosaccharide containing fraction. The monosaccharide fraction is then contacted with the recombinant bacteria of this invention under conditions effective for the fermentation of the glucose to ethanol. Details of the various fermentation techniques, conditions, and suitable microorganisms have been described, for example, by Wyman (1994, ibid) and Olsson and Hahn-Hagerdal (1996, ibid).

After completion of the fermentation, the ethanol may be recovered and optionally purified or distilled. Solid residue containing lignin may be discarded or burned as a fuel.

The following examples are intended only to further illustrate the invention and are not intended to limit the scope of the invention which is defined by the claims.

EXAMPLE 1

The production of recombinant *E. coli* in accordance with this Example is also described in Hespell et al. (1996, Appl. Environ. Microbiol., 62:4594–4597), the contents of which are incorporated by reference herein.

Materials and Methods

Bacterial strains, plasmids, and growth media. Strains *E.coli* B (ATTC 11303) and *E. coli* KO11 and plasmids pLOI295 and pLOI297 were obtained from L. 0. Ingram (University of Florida, Gainesville, Fla.). *E. coli* FMJ39 (K-12, F-, thr-1, leu-6, thi-1, lac Y, tonA22, straA, pfl-1, ldh) was received from D. P. Clark (Southern Illinois University, Carbondale, Ill.). All strains were grown on LB broth (10 g tryptone, 5 g yeast extract, 5 gm sodium chloride per 1 ) supplemented as indicated with Amp (50 to 100 $\mu$g/ml), Cm (40 $\mu$g/ml), or Tc (5 to 15 $\mu$g/ml) and arabinose or glucose. Antibiotics were added separately as filter-sterilized solutions and sugars as separately autoclaved or filter-sterilized solutions. For anaerobic growth of *E. coli*, LB broth also contained acetate (1 g/l) as an additional carbon source and the culture flasks or tubes were flushed with nitrogen gas and sealed with rubber stoppers.

Genetic procedures. Plasmids were routinely prepared from cells harvested from culture samples (1 to 10 ml) using routine procedures (Sambrook et al., 1989, Molecular cloning: a laboratory manual, 2nd ed., Cold Spring Harbor Laboratory Press, Cold Spring Harbor, N.Y.). The purity of plasmid preparations were verified by standard agarose gel electrophoresis of undigested and restriction endonuclease (Eco R1) digested plasmids. *E. coli* cells were transformed with plasmid DNA's (Hanahan et al., 1991, Methods Enzymology, 204:63–113) and recombinants were selected by plating on LB agar media containing Amp (pLOI295) or Tc (pLOI297).

High cell density fermentations. Mini-fermentors with automatic pH control were constructed and operated essentially as described by Beall et al. (Beall et al., 1991, Biotechnol. Bioeng., 38:296–303). Each 500 ml fleaker culture vessel contained 350 ml of LB broth containing 10% wt/vol sugar plus the appropriate antibiotic and was inoculated to an initial optical density (OD, 550 nm) of 0.5 using washed cells from a seed culture grown overnight. The culture was incubated at 35° C. and sampled (1–3 ml) periodically over 96 h incubation for measurements of OD, ethanol, sugars, organic acids, plasmid isolations, or viable cell counts.

Continuous culture fermentations. Long term stability of antibiotic resistance and ethanol production were assessed with a glucose-limited continuous culture. The chemostat consisted of a modified 2 1 Multigen fermentor (New Brunswick Scientific, New Brunswick, N.J.) containing 600 ml of LB broth maintained at 35° C. and sparged with nitrogen gas. The dilution rate was maintained at 0.1 h⁻¹ and the vessel pH was nearly constant (pH 6.2–6.4 ) over the entire run. The added LB medium contained 0.5% glucose and 15 $\mu$g/ml Tc and was pumped from a 201 reservoir. After 23 generations (7 days) the reservoir was replaced with one containing Tc-free medium and growth was continued for another 28 generations. Culture samples were taken twice daily to monitor OD, determine cell numbers, and for other analyses.

Analytical procedures. Ethanol and other alcohols were determined by gas liquid chromatography as described previously (Hespell, 1996, Curr. Microbiol., in press). Glucose and fermentation acids were determined by high pressure liquid chromatography using a refractive index detector and Aminex HPX-87H column (Bio-Rad, Richmond, Calif.) run at 65° C. and eluted (0.6 ml/min) with 5 mM sulfuric acid. Enzyme activities for PDC and ADH were measured (Conway et al., 1987, J. Bacteriol., 169:949–954; Conway et al., 1987, J. Bacteriol., 169:2591–2597) with cell-free extracts prepared from French pressure cell disrupted cell suspensions.

Results and Discussion

Construction of *E. coli* FBR1. *E. coli* FMJ39 was transformed with pLOI295 DNA and recombinant clones were screened using plates of LB agar medium containing 100

μg/ml Amp. About 10 clones were picked and verified for Amp resistance, for ability to grow anaerobically, and presence of plasmid with the same electrophoretic mobility as pLOI295. One of these clones, strain FBR1 was chosen for further work. This strain was grown aerobically or anaerobically with or without Amp (Table 1). Aerobic growth without Amp resulted in a very rapid loss of Amp resistant cells within 20 generations. Even with 50 μg/ml Amp, less than 1% of the cells remained resistant after 20 generations, but could be increased 50-fold or more when 100 μg/ml or higher Amp levels were used. In contrast, anaerobic growth led to almost all of the cells being Amp resistant, whether Amp was present or not in the medium. Plasmids with pLOI295 characteristics could be readily isolated from the cells grown anaerobically without Amp.

Figure 1:
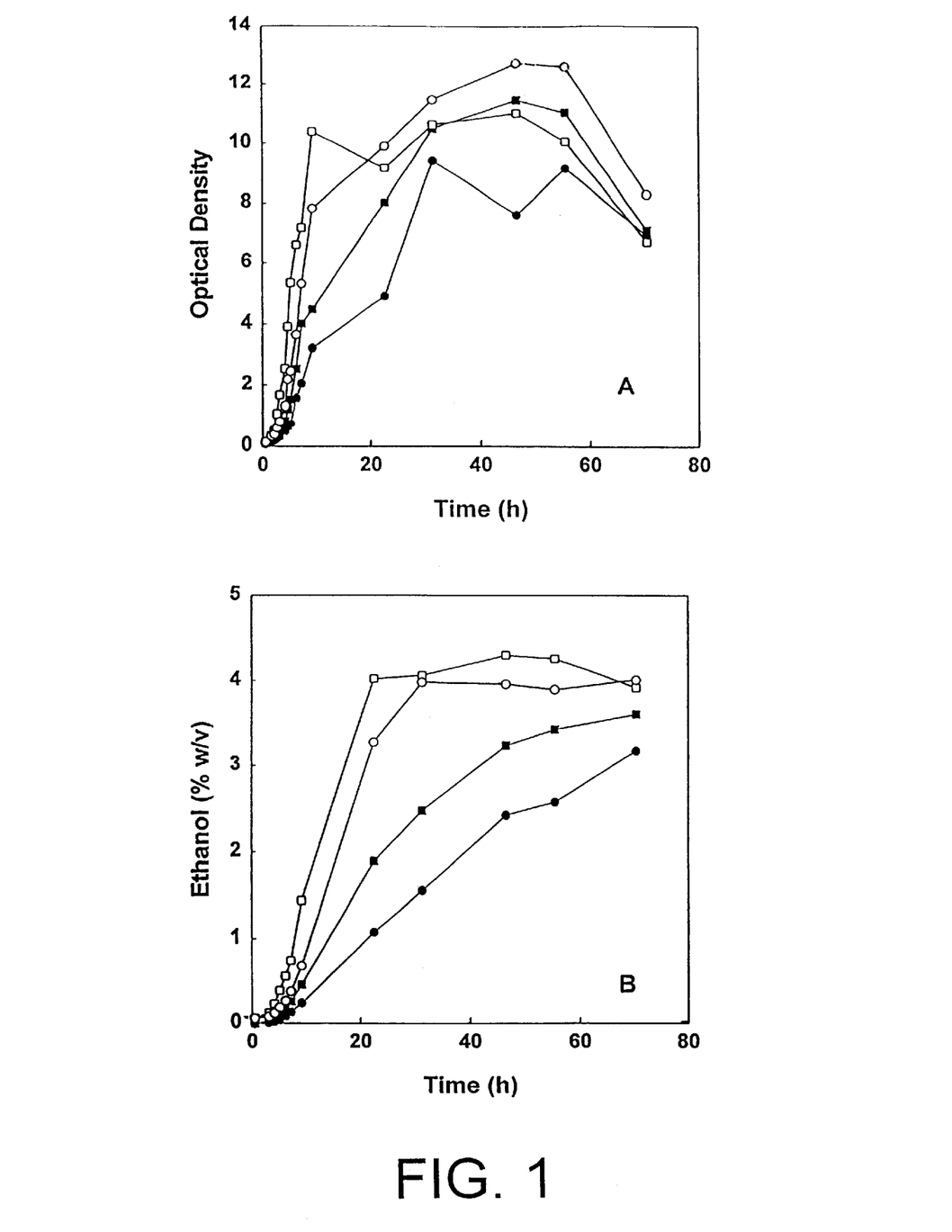
FIGS. 1A and 1B show the high cell density ethanol fermentations by *E. coli* strains FBR1 and KO11. Fleaker fermentors were inoculated with strain FBR1 (solid symbols) or strain KO11 (open symbols). The cultures were grown in the presence of air on LB medium containing 8% glucose (-□-,-■-) or arabinose (-○-,-●-) and 50 µg/ml Amp (FBR1) or 600 µg/ml Cm (KO11).

Ethanol production by E. coli FBR1. When grown in aerobic batch cultures with 5% glucose, E. coli FMJ39 produced about 0.16% ethanol after 48 h incubation whereas E. coli FBR1 produced about 0.9% wt/v ethanol after 24 h and 1.5% after 48 h incubation. Ethanol production and growth characteristics of E. coli FBR1 were then more carefully examined in fleaker fermentors (Beall et al., ibid) that have been routinely used to evaluate various PET operon-containing E. coli and other species (Table 2). Simultaneously, studies were conducted with E. coli KO11, which appears to be the best ethanol producing strain developed thus far (Ohta et al., ibid). Strain KO11 is a highly selected B strain with the PET operon chromosomally integrated apparently near or in the pfl gene, having a Tn10-induced fumarate reductase mutation to eliminate succinate formation, and possesses resistance to high levels (600 μg/ml) of Cm that concomitantly results in high ethanol production. Strain KO11 produced about 4.4% ethanol from glucose (Table 2) and time course measurements (FIG. 1) indicated this level was attained by 50 h. Similar ethanol levels and production rates were found with arabinose (a major sugar found in xylan hydrolysates of biomass) as the substrate. The other major xylan sugar, xylose, was not tested as parental strain FMJ39 cannot use it. These results compare very favorably with those found by Ingram and colleagues (Beall et al., ibid; Ohta et al., ibid). In comparison, the ethanol levels produced by E. coli strain FBR1 were about 10% less and yield was reduced (Table 2). In addition, ethanol productivity rates were slightly slower and maximal yields were attained at 75 h (FIG. 1). In other experiments, it was found that strain FBR1 produced about 1.0% succinate whereas strain KO11 formed less than 0.1% in batch cultures containing 5% glucose.

Construction of and ethanol production by E. coli FBR2. E. coli FMJ39 was transformed with pLOI297 to create strain E. coli FBR2. When grown either aerobically or anaerobically in serial batch cultures with Tc (15 μg/ml), essentially all of the cells were Tc resistant. In contrast, when grown without Tc in the medium, aerobic serial batch cultures contained less than 0.1% Tc resistant cells after 60 generations, but more than 30% were Tc resistant with anaerobic conditions. While unexpected, the apparent high percentage of Tc-sensitive anaerobic cells may be a result of several factors such as cell death occurring prior to production of Tc-inducible proteins and recovery on Tc-containing plate media. It also is possible that limited anaerobic growth might occur after plasmid loss due to residual PDC and ADH activities coupled with partial utilization of reducing equivalents during succinate formation.

Initial batch culture fermentations with 5% glucose resulted in production of about 1.6% wt/v ethanol after 48 h incubation by strain FBR2. While E. coli FMJ39 possessed less than 0.03 U/mg protein of adh or pdc activities, the levels of these enzymes in E. coli FBR2 were 1.7 U/mg and 6.2 U/mg, respectively. Ethanol production by E. coli FBR2 was determined in high cell density FLEAKER fermentors. For comparison, fermentations were also conducted with an E. coli B wild type strain which had been transformed with pLOI297. The results indicate that E. coli FBR2 produced higher levels of ethanol (4.4%) with better yields (0.46–0.48 g/g) than E. coli B (4.1%; 0.41 g/g). In addition, strain FBR2 also outperformed strain FBR1 (Table 2).

Figure 2:
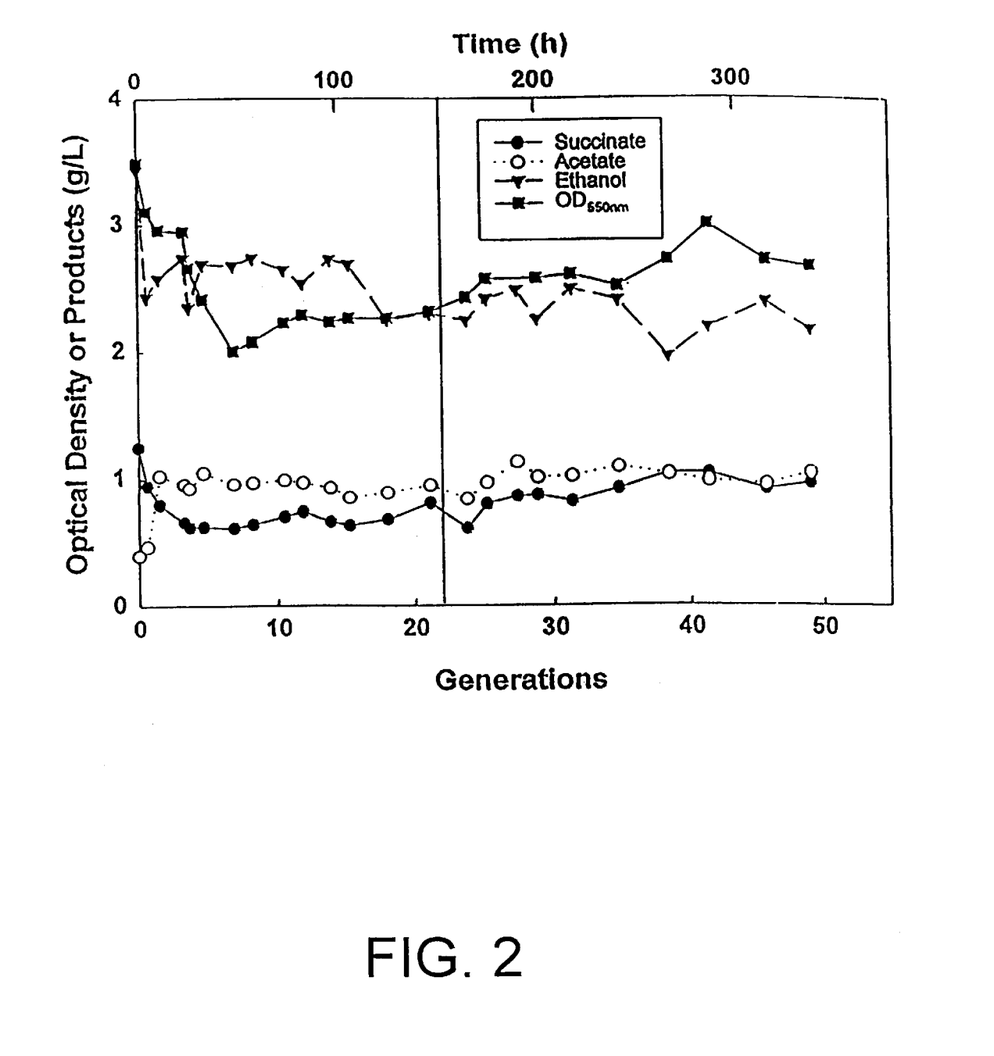
FIG. 2 shows the growth and product formation during long term, anaerobic continuous culture fermentation by *E. coli* FBR2. The culture was inoculated (1% v/v) and grown in batch for 24 h prior to initiation of continuous culture. After 23 generations (vertical bar) with 15 µg/ml Tc in LB medium with 0.5% wt/v glucose, the medium reservoir was replaced with one containing the same medium without Tc.

Continuous culture of E. coli FBR2. Lawford and Rousseau (1995, Appl. Biochem. Biotechnol., 57/58:277–292) showed that the presence of Tc and Amp in short-term continuous cultures of E. coli B with pLOI297, unexpectedly resulted in loss of ethanol production, implying loss of the plasmid. Using a long-term continuous culture, we examined the stability of strain FBR2, which also contains pLOI297, first in the presence (15 μg/ml) and after removal of Tc. During the first 3–4 days after inoculation, the microbial population appeared unstable as reflected in the rapid decline in optical density, but after 10 generations the optical density remained somewhat constant with a small rise after Tc removal (FIG. 2). Culture stability was also supported by the rather constant levels of acetate, ethanol, and succinate produced. However, a relatively long generation time (ca. 7 h) was maintained which probably induces some physiological stress. Nevertheless, microscopic examination of the cells revealed only single or pairs of rods.

Viable cell counts were determined on LB agar medium alone (total counts) or with 15 μg/ml Tc added (Tc resistant cell counts). Regardless of whether Tc was present or not, Tc resistant cells were generally 70–85% of the total cell counts. Based on two samples taken after 35 generations, cells were plated on media containing only 5 μg/ml Tc and in both cases the cell counts were about 15% higher than the counts on 15 μg/ml Tc plates. As noted earlier, these data might suggest that some viability losses may occur on the plates until the Tc-induced proteins are fully expressed. Overall, Tc resistance was maintained at high levels in the Tc-free continuous culture. In addition, the appropriate size plasmid could be recovered from FBR2 culture samples.

Ethanol production and antibiotic resistance after continuous culture. After about 15 days or 55 generations (32 after Tc removal), samples were taken from the continuous culture and used to inoculate (1% v/v) anaerobic batch cultures containing no Tc. These cultures produced high levels of ethanol at high rates and essentially all cells were resistant to Amp, the other antibiotic gene on pLOI297 in strain FBR2. These trends continued even after three serial transfers (Table 3). Simultaneously, cultures were inoculated with cells from fresh batch stock cultures and yielded similar results. To assess maximal ethanol production, pH-controlled anaerobic FLEAKER fermentors also inoculated with the same cells from the continuous culture. These fermentors produced about 3.6% ethanol as compared to 4.1% with fermentors simultaneously inoculated from fresh stock cultures. These data clearly indicate that high levels of ethanol production and genetic stability can be maintained by E. coli FBR2 after prolonged anaerobic growth in the absence of antibiotics with glucose-limited continuous culture followed by several batch cultures.

Thus the requirement for antibiotics, a major economic and environmental drawback to use of PET operon-containing, ethanologenic E. coli strains, no longer exists, provided anaerobic growth conditions are used.

EXAMPLE 2

Materials and Methods

Bacterial strains, plasmid, and growth media. *E.coli* strain FMJ39 (K-12) [F- thr-1 leu 6 thi-1 lacY tonA22 straA pfl-1 ldh] was received from D. P. Clark (Southern Illinois University, Carbondale, Ill. and *E.coli* strain $C_{600}$ (Appleyard, 1954, Genetics, 39:440–452) was received from the ARS Culture Collection, Peoria, Ill. Plasmid pLOI297 was obtained from L.O. Ingram (University of Florida, Gainesville, Fla.). Strains were routinely grown on LB broth (10 g tryptone, 5 g of yeast extract, 5 g of sodium chloride per liter) supplemented as indicated with Tet (10 µg/ml) and either L-arabinose, D-glucose, or D-xylose. Antibiotics were added separately as filter-sterilized solutions, and sugars were added separately as autoclaved solutions.

MacConkey solid medium (Difco, MI) supplemented with xylose (5 g/l) was used for identifying xylose utilizing mutants. Aerobic medium used for testing plasmid stability contained LB prepared without NaCl and supplemented with 4 g/l glucose or xylose, and PIPES buffer (0.1 M, adjusted to pH =7 with NaOH); solid medium also contained 15 g/l agar. For anaerobic growth of *E. coli,* LB broth contained either glucose or xylose (4 g/l), acetate (1 g/l) as an additional carbon source, sodium bicarbonate (4 g/l) as a buffer, and cysteine HCL (0.5 g/l) as an oxygen scavenger. Anaerobic medium was flushed with a 20% $CO_2$ and 80% $N_2$ gas mixture and sealed with butyl rubber stoppers as previously described [Hespell, Isolation of anaerobic microorganisms, In: *Isolation of Biotechnological Organisms from Nature,* Labeda (Ed.), McGraw-Hill Publishing Co., St. Louis, 1990, 117–140]. The pH of the buffered medium was 7.0.

Culture growth conditions and testing for plasmid maintenance. Unless stated otherwise, cultures were incubated at 37° C. Aerobic cultures were grown in Erlenmeyer flasks capped with a two fold milk filter, filled with medium to a liquid to flask ratio of 1:10 v/v and agitated at 300 rpm. Anaerobic cultures were grown in either test tubes or serum bottles capped with butyl rubber caps and agitated at 90 rpm. Anaerobic cultures used for determining specific growth rates were incubated in a water bath set to 35° C. and vortexed previous to measuring optical density.

Plasmid maintenance in liquid cultures of FBR3 was measured by replica plating colonies grown on non-selective plates onto selective plates. Aliquots from liquid cultures were serially diluted and plated on aerobic LB medium supplemented with either glucose or xylose. Plates were incubated for 12–16 h at 30° C. Fifty randomly selected colonies were transferred to a plate containing similar medium supplemented with Tet; plasmid pLOI297 contains a Tct resistance gene. The selection plates were incubated for 18 h before checking for colony formation.

Genetic procedures. Plasmids were prepared from cells harvested from culture samples (1 to 10 ml) by routine procedures (Sambrook et al., ibid). The purity of plasmid preparations was verified by standard agarose gel electrophoresis of undigested and restriction endonuclease (Eco RI)-digested plasmid. *E. coli* cells were transformed with plasmid DNAs (Hanahan et al., ibid), and recombinants were selected by plating on LB agar medium containing Tet.

Batch fermentations of arabinose, glucose, and xylose. Minifermentors with automatic pH control were constructed and operated essentially as described previously (Beall et al., ibid; Dien et al., 1997, World J. Microbiol. Biotechnol., in press). Each 500-ml FLEAKER culture vessel contained 300 ml of LB broth supplemented with 10% w/v total sugar and 0.02% (v/v) antifoam 289 (Sigma, MO). Medium and vessels were bubbled with $N_2$ for 1 h subsequent to inoculation. Vessels were inoculated with a 5% v/v inoculum from an anaerobic culture grown over-night at 35° C. with xylose as the carbon source. The cultures were incubated at 35° C. and sampled (1.5 ml) periodically over 96 h of fermentation for measurements of $OD_{550}$, ethanol, sugars, and organic acids. The pH set point of 6.5 was maintained by addition of a concentrated base solution containing 2.5 N of NaOH and KOH each for a total base concentration of 5 N.

Analytical procedures. Optical density was monitored through culture turbidity at 550 nm. Head space gases were detected using a gas liquid chromatograph (Hewlett Packard Co, DL) equipped with a TCD detector. The column used was a carbo sieve G (100/120 Mesh) column (Supelco, PA) and the carrier gas was Argon. Head space gas samples were run isothermally with an injector and oven temperature of 170° C. and a detector temperature of 220° C. Amounts of ethanol were determined by gas liquid chromatography as described previously (Dien et al, 1997, ibid). Amounts of sugars and fermentation-generated organic acids were determined by high-pressure liquid chromatography (HPLC) using an Aminex HPC-87H column (Bio-Rad, Richmond, Calif.) and refractive index detector. Samples were run at 65° C. and eluted at 0.6 ml/m with 5 mM sulfuric acid.

Calculation of fermentation parameters. Ethanol and biomass yields were calculated by dividing either the amount (g) of ethanol or biomass (g) produced by total sugar added (g) to medium. Biomass production was determined from optical density measurements; 1.0 optical density at 550 nm was determined to be equal to a concentration of 0.30 mg/ml cell dry weight (data not shown). Volumetric ethanol production rates ($V_{ETOH}$) were calculated from the increase in ethanol concentration between subsequent samples. Biomass yields were calculated by dividing grams of biomass formed by the total amount of sugar added. Both yields and VETOH were corrected for the dilution of the culture from inoculation and automatic base additions needed to maintain pH 6.5.

A carbon balance was carried out based upon consumed sugars (arabinose, glucose, and xylose/galactose) and products formed (acetate, biomass, ethanol, lactate, and succinate). It was assumed the amount of carbon dioxide produced was equimolar to the ethanol and acetate minus the succinate production (Clark, 1989, FEMS Microbiol. Reviews, 63:223–234). The dried *E. coli* biomass was assumed to be 45% w/w carbon (Bauer and Ziv, 1976, Biotechnol. Bioeng., 28:81–94). Final product and sugar concentrations were corrected for dilution by base addition.

Results

Isolation of xylose utilizing. The FMJ39 strain received from D. P. Clark did not grow anaerobically on LB medium supplemented with xylose. However, spontaneous xylose utilizing mutants were isolated using McConkey plates supplemented with xylose. McConkey plates contain pH sensitive dyes; colonies that metabolized xylose were identified by pH changes to the surrounding medium. Four xylose utilizing strains were isolated and transformed with plasmid pLOI297, which contains the PET operon. Each of these strains was tested for ethanol fermentation rates and yields in pH controlled fermentations of xylose and were determined to all perform equally well (data not shown). One of these strains (FBR3) was chosen for further study.

Maintenance of pLOI297 in repeated batch cultures. Plasmid stability for FBR3 was tested using serial batch cultures. Cultures were grown anaerobically and aerobically in media supplemented with glucose and xylose. Cultures were transferred every 12 h using a 1% v/v inoculum for the glucose grown culture and a 2% v/v for the xylose grown culture. The ratio of cells carrying and not carrying the plasmid pLOI297 was measured after every other transfer. When grown anaerobically on glucose or xylose, the culture maintained the plasmid in an average of 97% and 98% of the cells, respectively (Table 4). However, when grown aerobically, the plasmid quickly disappeared from the culture.

Figure 3:
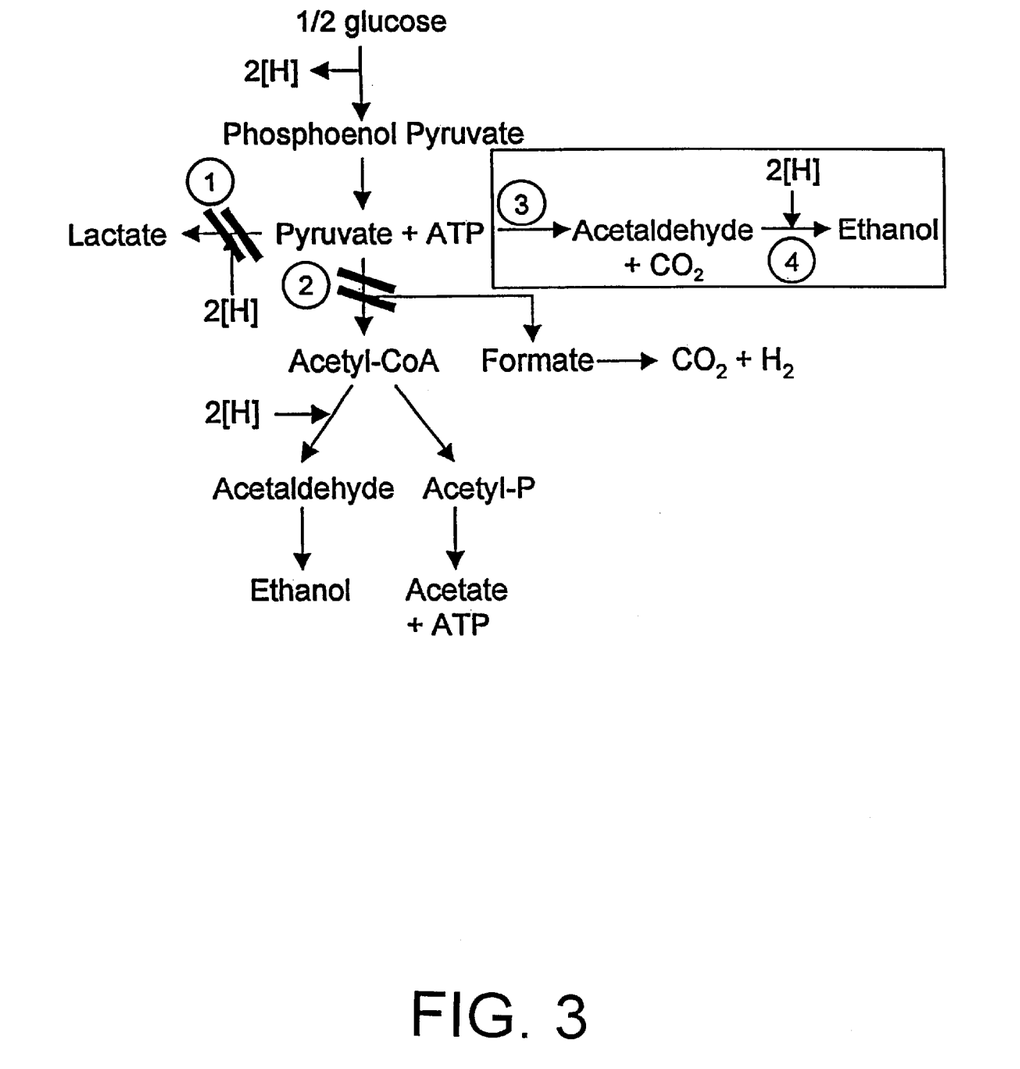
FIG. 3 shows the fermentation pathway for *E. coli* FBR3. Strain FMJ39 cannot grow anaerobically because it is unable to fermentatively reduce pyruvate and regenerate the NAD$^+$ used in converting hexose and pentose sugars into pyruvate. The pyruvate cannot be reduced because the strain's lactate dehydrogenase (1) and pyruvate formate lyase (2) activities have been deleted. When transformed with pLOI297, FMJ39 can grow anaerobically because the plasmid encodes for adh (3) and pdc (4) activities, which allow for pyruvate to be reduced to ethanol. Deleted enzyme activities are signified by double slashes and added ethanol production pathway (adh and pdc) is boxed. See text for further details.

Testing stability of pfl mutation. As a further control, we also tested the stability of the pfl mutation in the culture by measuring $H_2$ production. The pfl protein converts pyruvate to formate and acetyl-CoA (FIG. 3). Some of the formate is converted into $CO_2$ and $H_2$ by the activity of formate dehydrogenase (fdh). Therefore, detection of $H_2$ production is an indirect measure of pfl activity.

To test the utility of this assay for detecting pfl activity, $E.$ $coli$ strain $C_{600}$, ancestral strain of strain FMJ39 (Varenne et al., ibid) and FBR3 were grown overnight anaerobically. While strain $C_{600}$ produced $H_2$ and $CO_2$, FBR3 only produced $CO_2$. As a control to ensure the absence of $H_2$ is due to an absence of pfl activity and not fdh activity, FBR3 was once again grown overnight anaerobically, but this time sodium formate (0.1% w/v) was added to the culture. In contrast, to the previous result, $H_2$ was now detected in the head space gases, indicating the presence of fdh activity.

Next, strains $C_{600}$ and FBR3 were serially transferred 10 times (2/day) under anaerobic growth conditions; $C_{600}$ was grown on glucose and FBR3 on glucose and xylose. Each culture was tested for $H_2$ production immediately after transferring the culture. In each case, strain $C_{600}$ produced $H_2$ and FBR3 produced no detectable amounts of $H_2$ (Table 5). Therefore, when grown anaerobically in repeated batch cultures, the pfl mutation was maintained by the culture.

Specific growth rates. Specific growth rates were determined for strain FBR3 grown anaerobically on arabinose, glucose, and xylose (Table 6) at 35° C. Cell growth was monitored by optical density. All strains grew fastest on glucose and slowest on xylose. Furthermore, the growth of strain FBR3 was approximately 60% slower than strain $C_{600}$ on glucose. The specific growth rate of FBR2 on glucose was similar to that of FBR3 (Table 6).

Batch fermentations of arabinose, glucose, and xylose. A culture of FBR3 that had been transferred 16 times on anaerobic medium supplemented with xylose was further tested in high sugar concentration pH controlled batch fermentations to determine if it would still efficiently convert hexose and pentose sugars into ethanol. The batch fermentations contained LB supplemented with 10% w/v arabinose, glucose, xylose, or mixture of these sugars (2% w/v arabinose, 4% w/v glucose, and 4% w/v xylose); no cysteine or antibiotic 5 was added to the media. The sugar mixture medium contained sugar concentrations typical of lignocellulosic corn fiber hydrolysate generated in this laboratory (Dien et al., 1997, ibid). Fermentation data are summarized by FIG. 4 and Table 7.

Figure 4:
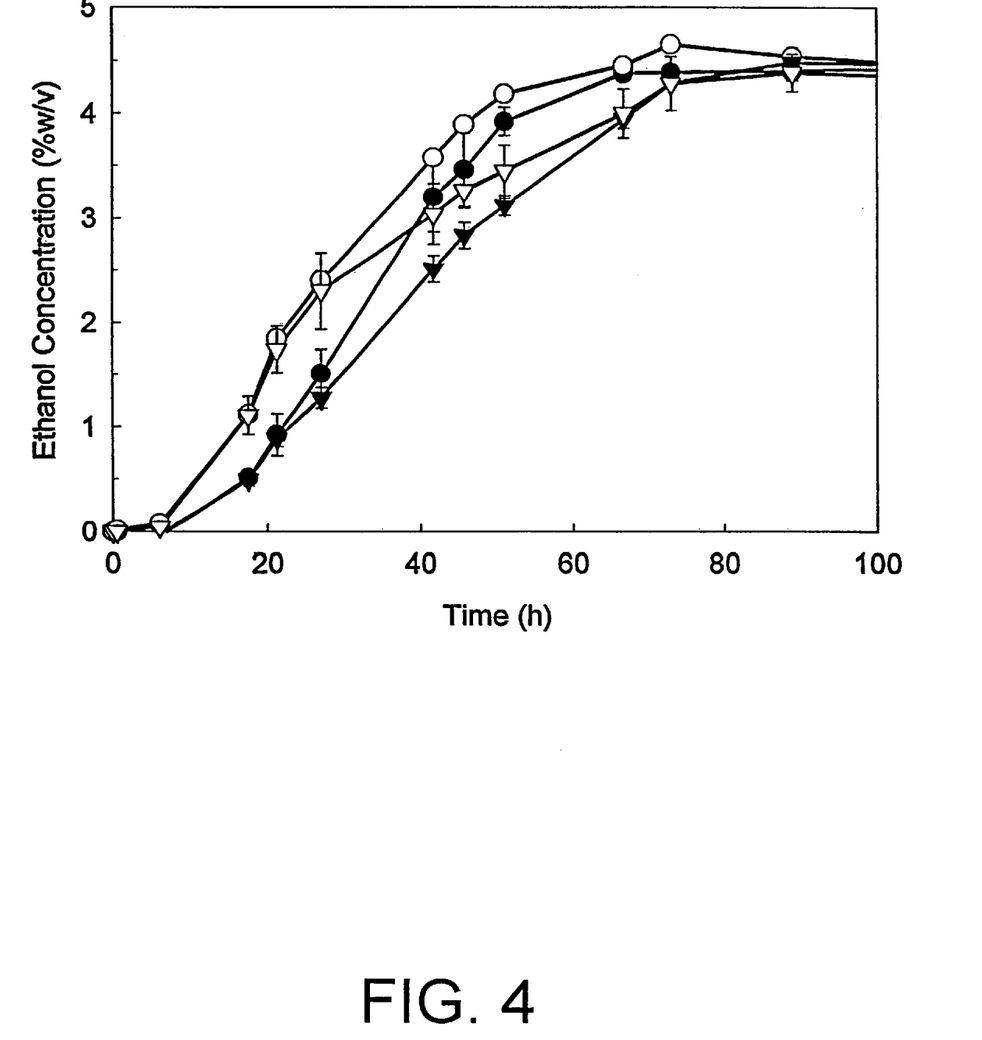
FIG. 4 shows the ethanol measurements from pH controlled batch fermentations of 10% w/v sugars. The cultures were grown in micro-aerophilic cultures on LB medium containing Tct (10 µg/ml) and either ● arabinose, ○ glucose, ▼0 xylose, or ▽0 mixed sugars (arabinose 2% w/v, glucose 4% w/v, and xylose 4% w/v). Each fermentation was run in duplicate and each point is the average of two runs.
Figure 5:
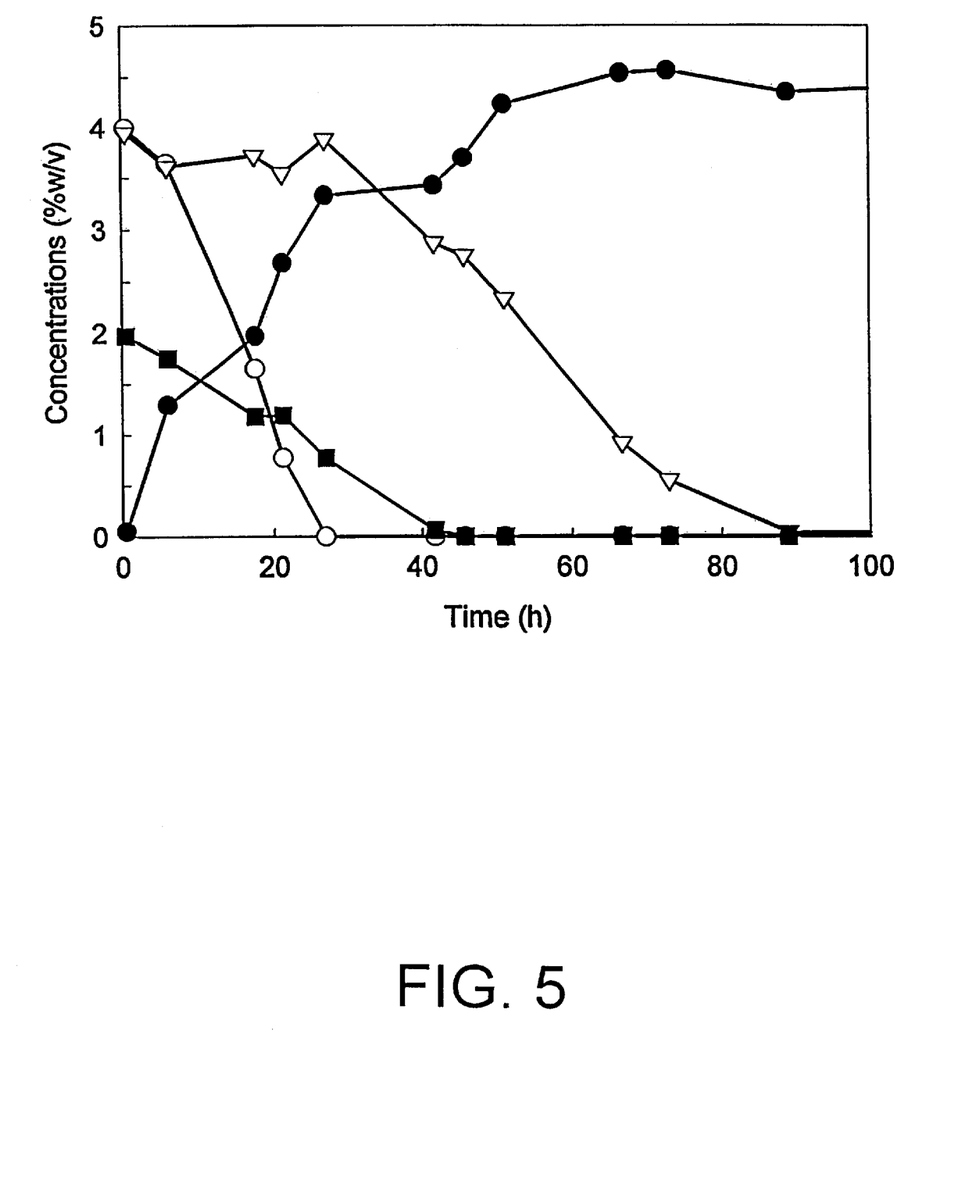
FIG. 5 shows the ethanol fermentation of mixed sugars by *E. coli* strain FBR3. Symbols: ■ arabinose, ● ethanol, ○ glucose, and ▽ xylose.

Maximal ethanol concentrations were reached in approximately 70 h (FIG. 4). They ranged in value from 4.38% w/v to 4.66% w/v and were higher for pentose fermentations than glucose. Sugars were completely metabolized in all the fermentations. When fermenting a mixture of sugars, FBR3 used glucose preferentially followed by arabinose; xylose was not metabolized until glucose was completely consumed (FIG. 5). Biomass yields, which were calculated from optical density measurements, ranged from 0.43–0.47 g of biomass per g of sugar and were higher for glucose than for pentose fermentations.

Ethanol yields were similar for each of the fermentations: 0.46–0.47 g of ethanol per g of sugar or 90–91% of the maximum theoretical yield (Table 7). Maximum $V_{EtOHs}$ were 0.86 g/l/h-1.20 g/l/h and nearly equal for glucose and arabinose fermentations; xylose fermentations were 30% slower. Ethanol productivity slowed for the mixed sugar fermentation after the arabinose and glucose were completely consumed.

The amount of base (2.5 N KOH+2.5 N NaOH) added to the cultures to maintain the set point pH was 153–173 mMol per 1 of culture (Table 7). Minor amounts of lactate and succinate were produced (Table 7), indicating that some ldh activity might still be present. No acetate or formate were detected, indicating the complete inactivation of the pfl mutation (FIG. 3). Over 95% of the consumed sugars (Table 7, last column) was accounted for as ethanol, organic acids, and biomass.

Each fermentation was sampled 70 h after inoculation and the cells tested for maintenance of plasmid pLOI297. It was determined 97–99% of the cells in the fermentation had maintained the plasmid (Table 5). Furthermore, plasmid DNA isolated from each fermentation was found to be the expected size (data not shown).

Discussion

In Example 1 we showed that the pLOI297 plasmid is positively selected for in anaerobic repeated batch and continuous cultures of FBR2. We also found that strain FBR2 did not grow on xylose. However, spontaneous mutants of FBR2 that did use xylose were easily isolated on MacConkey solid medium supplemented with xylose. One of these mutants (FBR3) was selected for further study.

The plasmid stability of FBR3 has been tested in repeated batch cultures with glucose or xylose. When grown anaerobically for 10 transfers an average of 97 and 98%—for glucose and xylose supplemented cultures, respectively—maintained the plasmid. These results are what were expected. When the culture is grown anaerobically, the cells are under selective pressure to maintain the plasmid because cells that lose the plasmid are unable to grow anaerobically. While under aerobic conditions, the cells do need the plasmid to grow because they metabolize glucose and xylose via the oxidative pathway. Therefore, the plasmid is quickly lost when the culture is grown aerobically. That some cells, when grown anaerobically still manage to loose the plasmid might be accounted for by either cytoplasmic inheritance or plasmid lost when growing into colonies on the first plating.

The plasmid stability experiment results are particularly significant because the cells were cultured under carbon limited conditions, which is thought to lead to phenotypic instability in KO11 cultures (Dr. Ingram, personal communication). In contrast, to anaerobic conditions, pLOI297 was readily lost when the cells were cultured in repeated aerobic cultures. Thereby, demonstrating that the PET operon is selected for under anaerobic growth conditions.

The stability of the pfl mutation in repeated batch cultures for cells grown on either glucose or xylose was tested by detecting for $H_2$ production. Hydrogen gas production is a sensitive assay for pfl activity. No $H_2$ was detected in any of the cultures used for the plasmid stability experiment described above. In contrast, $H_2$ production was detected in each of the control *E. coli* strain ($C_{600}$) known to have pfl activity.

Even after *E. coli* strain FBR3 had been transferred 16 times (approximately 90 doublings) without antibiotics, it fermented hexoses and pentoses as well as cultures of *E. coli* KO11 that had not been repeatedly transferred. Ethanol fermentations were carried out using LB supplemented with either 10% w/v arabinose, glucose, xylose, or a mixture of these sugars under similar conditions used for strain KO11 fermentations in this laboratory (Dien et al., 1997, ibid). Ethanol yields for strain FBR3 varied from 0.46–0.47 g ethanol per g sugar, equivalent to yields measured for strain KO11 (0.44–0.47 g ethanol per g sugar (Dien et al., 1997, ibid). Biomass yields (g/l) and base addition, for maintaining the pH set point, were also similar for both strains (this Example and Dien et al., 1997, ibid). Only maximum ethnol productivity differed significantly between these strains (e.g., 56% slower for xylose fermentations with strain FBR3). However, the slower ethanol productivity of strain FBR3 compared to strain KO11 would cease to be a disadvantage if FBR3 cells could be recycled because higher cell densities would more than compensate for the lower productivity.

It is understood that the foregoing detailed description is given merely by way of illustration and that modifications and variations may be made therein without departing from the spirit and scope of the invention.

TABLE 1

Stability of AMP resistance and pet operon in *E. coli* FBR1

| No. of generations/ days and plating medium | Viable cell count ($10^5$) under the following growth conditions: | | | |
|---|---|---|---|---|
| | Aerobic | Aerobic + AMP | Anaerobic | Anaerobic + AMP |
| 20/3 | | | | |
| LB | 2,500 | 400 | 200 | 500 |
| LB + AMP | 1.7 | 7.8 | 130 | 130 |
| 40/6 | | | | |
| LB | 8,200 | 8,300 | 600 | 630 |
| LB + AMP | 1.3 | 5.0 | 470 | 690 |
| 60/9 | | | | |
| LB | 5,400 | 7,200 | 730 | 1,300 |
| LB + AMP | 1.0 | 7.1 | 730 | 1,200 |

[a]Batch cultures were transferred (1% [vol/vol]) on a daily basis with LB broth, with (50 μg/ml) or without AMP added, and were grown under an aerobic (air) or anaerobic (nitrogen) atmosphere.

TABLE 2

Ethanol fermentations by *E. coli* KO11 and *E. coli* FBR1[a]

| Strain | Sugar (10%) | OD | Generation time (min) | Amt of ethanol (% [wt/vol]) | Ethanol yield (g/g) |
|---|---|---|---|---|---|
| KO11 | Glucose | 11.6 | 69 | 4.36 | 0.47 |
| KO11 | Arabinose | 12.3 | 83 | 4.24 | 0.45 |

TABLE 2-continued

Ethanol fermentations by *E. coli* KO11 and *E. coli* FBR1[a]

| Strain | Sugar (10%) | OD | Generation time (min) | Amt of ethanol (% [wt/vol]) | Ethanol yield (g/g) |
|---|---|---|---|---|---|
| FBR1 | Glucose | 12.7 | 74 | 3.85 | 0.41 |
| FBR1 | Arabinose | 9.6 | 86 | 3.51 | 0.37 |

[a]Fermentations were carried out in fleaker fermentors containing LB broth initially supplemented with 600 μg of CHL (KO11) or 50 μg of AMP (FBR1) per ml.

TABLE 3

Serial batch culture fermentations by *E. coli* FBR2[a]

| | Amt of ethanol (% [wt/vol]) | | Viable cell Counts ($10^7$) | |
|---|---|---|---|---|
| Series/transfer | 24 h | 48 h | LB | LB + AMP |
| A/1 | 1.15 | 2.32 | | 27 |
| A/2 | 1.12 | 2.23 | 29 | 24 |
| A/3 | 1.44 | 3.15 | 41 | 41 |
| B/1 | 2.07 | 3.30 | | 160 |
| B/2 | 1.80 | 2.75 | 130 | 130 |
| B/3 | 2.00 | 3.05 | 90 | 99 |

[a]Anaerobic LB broth with 10% glucose plus 0.2 M $NaPO_4$ (pH 7.0) inoculated (1% [vol/vol]) with cells after 55 generations in continuous culture (series A) or with cells from fresh stock cultures (series B).

TABLE 4

Plasmid maintenance by strain FBR3 under anaerobic growth conditions

| | Glucose | | Xylose | |
|---|---|---|---|---|
| Transfers | Anaerobic | Aerobic | Anaerobic | Aerobic |
| | % Colonies that grew on selective plate vs Colonies plated | | | |
| 100 | | 86 | 100 | 94 |
| 2 | 98 | 60 | 100 | 60 |
| 4 | 100 | 0 | 98 | 4 |
| 6 | 100 | 0 | 96 | 0 |
| 8 | 88 | 0 | 98 | 0 |
| 10 | 98 | 0 | 98 | 0 |

TABLE 5

Stability of pfl mutation in serial batches for FBR3

| Transfers | Strain $C_{600}$[1] | Glucose | Xylose |
|---|---|---|---|
| | Hydrogen detected (+) or not detected (−) | | |
| 1 | + | − | − |
| 2 | + | − | − |
| 3 | + | − | − |
| 4 | + | − | − |
| 5 | + | − | − |
| 6 | + | − | − |
| 7 | + | − | − |
| 8 | + | − | − |
| 9 | + | − | − |
| 10 | + | − | − |

Notes:
[1]*E. Coli* strain $C_{600}$ was used as a positive $H_2$ control and was grown on glucose.

TABLE 6

Specific growth of anaerobic E. coli cultures on various sugars

| Strain | Sugar | $\mu$ (1/h)[1] |
|---|---|---|
| C600 | Glucose | 1.27 ± 0.04 |
| FBR2 | Glucose | 0.76 ± 0.00 |
| FBR3 | Arabinose | 0.55 ± 0.01 |
| FBR3 | Glucose | 0.78 ± 0.03 |
| FBR3 | Xylose | 0.47 ± 0.07 |

[1]Average of duplicate runs.

TABLE 7

Results from pH controlled batch fermentations[1]

| Sugar | Biomass Yield (g/g) | Maximum Ethanol (% w/v) | Ye/s[2] (g/g) | $V_{EtOH}$[3] (g/l/h) | Base Addition (mmoles/l) | Plasmid[4] Stability (%) | Carbon Recovery (%) |
|---|---|---|---|---|---|---|---|
| Arabinose | 0.46 ± 0.02 | 4.44 ± 0.06 | 0.46 ± 000 | 1.20 ± 0.07 | 173 ± 13 | 99 ± 1 | 96 ± 1 |
| Glucose | 0.47 ± 0.01 | 4.66 ± 0.03 | 0.47 ± 0.00 | 1.18 ± 0.02 | 153 ± 20 | 98 ± 2 | 98 ± 0 |
| Xylose | 0.43 ± 0.01 | 4.48 ± 0.05 | 0.46 ± 0.01 | 0.86 ± 0.02 | 153 ± 07 | 98 ± 2 | 97 ± 0 |
| Mixed Sugars | 0.44 ± 0.03 | 4.38 ± 0.18 | 0.47 ± 0.01 | 1.14 ± 0.14 | 167 ± 47 | 97 ± 1 | 99 ± 1 |

[1]Results are average of duplicate runs.
[2]Yield of ethanol (g) per total consumed sugar(s) (g).
[3]Maximum volumetric production rate of ethanol.
[4]Percentage of cells carryng pLOI297 at completion of fermentation.

TABLE 8

Organic acids produced during Fleaker ® fermentation[1]

| Sugar | Acetate (g/l) | Formate (g/l) | Lactate (g/l) | Succinate (g/l) |
|---|---|---|---|---|
| Arabinose | nd[2] | nd | 3.4 ± 0.2 | 5.2 ± 0.1 |
| Glucose | nd | nd | 3.6 ± 0.2 | 3.9 ± 0.1 |
| Xylose | nd | nd | 3.2 ± 0.2 | 4.4 ± 0.1 |
| Mixed Sugars | nd | nd | 1.3 ± 0.4 | 5.8 ± 0.4 |

[1]Results are average of duplicate runs.
[2]nd (not detectable).

We claim:

1. A recombinant bacterium comprising a mutant bacterium which has been transformed with heterologous DNA to produce the recombinant bacterium,
    wherein said mutant bacterium comprises mutations that decrease the activities of lactate dehydrogenase and pyruvate formate lyase to the extent that the mutant bacterium is rendered incapable of anaerobic fermentative growth,
    wherein said heterologous DNA encodes alcohol dehvdrogenase and pyruvate decarboxylase, and
    wherein said recombinant bacterium is capable of anaerobic growth and expresses said heterologous DNA at a sufficient level for the recombinant bacterium to produce ethanol as a primary fermentation product.

2. The recombinant bacterium of claim 1 wherein said bacterium is a gram negative bacterium.

3. The recombinant bacterium of claim 2 selected from the group consisting of Escherichia, Erwinia, and Klebsiella species.

4. The recombinant bacterium of claim 1 wherein the parent strain of said mutant bacterium is a facultative anaerobe.

5. The recombinant bacterium of claim 1 wherein said mutant bacterium is unable to fermentatively reduce pyruvate.

6. The recombinant bacterium of claim 1 further comprising a gene coding for a polysaccharase.

7. The recombinant bacterium of claim 1 further comprising a gene encoding a protein which enables said recombinant bacterium to transport and metabolize an oligosaccharide.

8. The recombinant bacterium of claim 1 wherein said heterologous DNA coding for alcohol dehydrogenase and pyruvate decarboxylase is on a plasmid within said recombinant bacterium.

9. A method for producing ethanol comprising contacting a recombinant bacterium with a fermentable substrate in an anaerobic environment without antibiotics in an amount and under conditions effective to produce ethanol from said substrate,
    wherein said recombinant bacterium comprises a mutant bacterium which has been transformed with heterologous DNA to produce the recombinant bacterium,
    wherein said mutant bacterium comprises mutations that decrease activities required for fermentative reduction of pyruvate to the extent that the mutant bacterium is rendered incapable of anaerobic fermentative growth,
    wherein said heterologous DNA encodes alcohol dehydrogenase and pyruvate decarboxylase, and
    wherein said recombinant bacterium is capable of anaerobic growth and expresses said heterologous DNA at a sufficient level for the recombinant bacterium to produce ethanol as a primary fermentation product.

10. A recombinant bacterium comprising a mutant bacterium which has been transformed with heterologous DNA to produce the recombinant bacterium,
    wherein said mutant bacterium comprises mutations that decrease activities required for fermentative reduction of pyruvate to the extent that the mutant bacterium is rendered incapable of anaerobic fermentative growth and incapable of anaerobic growth on culture media having glucose with acetate as carbohydrates,
    wherein said heterologous DNA encodes alcohol dehydrogenase and pyruvate decarboxylase, and
    wherein said recombinant bacterium is capable of anaerobic growth and expresses said heterologous DNA at a sufficient level for the recombinant bacterium to produce ethanol as a primary fermentation product.

* * * * *